(12) United States Patent
Iba et al.

(10) Patent No.: US 6,596,929 B2
(45) Date of Patent: Jul. 22, 2003

(54) ELEMENT INDUCIBLE IN RESPONSE TO INJURY, A PROMOTER INDUCIBLE IN RESPONSE TO INJURY AND A TRANSGENIC PLANT

(75) Inventors: Koh Iba, Fukuoka (JP); Takiko Shimada, Ishikawa (JP); Tomonobu Kusano, Ikoma (JP)

(73) Assignee: Kyushu University, Fukuoka (JP)

( * ) Notice: Subject to any disclaimer, the term of this patent is extended or adjusted under 35 U.S.C. 154(b) by 0 days.

(21) Appl. No.: 09/293,836

(22) Filed: Apr. 19, 1999

(65) Prior Publication Data

US 2002/0066119 A1 May 30, 2002

(51) Int. Cl.[7] .................. C12N 15/82; A01H 5/00; C07H 21/04
(52) U.S. Cl. ............. 800/287; 800/298; 536/24.1
(58) Field of Search .................. 800/287, 278, 800/298, 320, 320.1, 320.2, 320.3; 536/24.1; 435/468

(56) References Cited

PUBLICATIONS

Benfey et al, "The Cauliflower Mosaic Virus 35S Promoter: Combinatorial Regulation of Transcription in Plants", Nov. 1990, Science vol. 250, pp. 959–966.*

Kim et al, "A 20 nucleotide upstream element is essential for the nopaline synthase (nos) promoter activity", 1994, Plant Molecular Biology, vol. 24, pp. 105–117.*

Nishiuchi et al. Palnt Molecular Biology, vol. 29, No. 3, pp. 599–609.* vol. 124, 1997, Ref. 108756u (Chemical Abstract).

vol. 128, 1998, Ref. 32415s (Chemical Abstract).

vol. 126, 1997, Ref. 208174n (Chemical Abstract).

vol. 111, 1998, Roles of plastid omega 3 fatty acid desaturases in defense response of higher plants, (Journal of Plant Research)—Abstract only.

* cited by examiner

Primary Examiner—Elizabeth F. McElwain
Assistant Examiner—Cynthia Collins
(74) Attorney, Agent, or Firm—Burns, Doane, Swecker & Mathis, LLP

(57) ABSTRACT

To develop a promoter inducible in response to injury, this invention provides an injury-inducible element, which may be added to a promoter.

The invention provides an injury-inducible element that is a base sequence referred to as nucleotide numbers from −611 to −629 SEQ ID No: 1.

8 Claims, 2 Drawing Sheets

FIG. 1 a promotor sequence of FAD7 gene

```
                                              ┌─Nco I
-853 AAATTCATGC GGAATCAGAG AACGTTACCA TGGTGGGATG AAGATGAATT GCGGCCCTGT

-793 AAAGTTTTAG TCTTGTTCAA TAGATTGCAC AAAGAAAGTA AACAAACAAC AACAAAAAAA

-733 AAGACTGTAG AAAAGAAAAA AAAAAAGGAT AATCATAACG GAATCTTTAA TTTACCAGCG

-673 CGATTAAGGA CCTCAGATTG TTGTTCGGTG CCATGATCGG ATATTAGGGT TCGTTCGCTC
                                              GATA motif
-613 TTCTTCTTCT TTGTCTATAC GCGATTTGTG AGAATAAAAA AGGTCGGATC TTTTGAGAGT
                                              ┌─Apa I
-553 TCTGTAGTTT AATGGGCTTA TACTATTGGG CCCTAGCCCA AATGAGCGAC ACTATTGTTC

-493 ATTTTGTACA AATCTCTTGG GCTAATTTAT TTCAGGCTGA CCAACTAATT TGGTCAACTA

-433 GTTGGGTTTG GCATGTTTAA TTTCAATTTC CACTTGGTTC AATTTTTATG TTCACCGTCC
        ┌─Spc I       G·box·like motif        Inverted G·box·like motif
-373 ATGTAACTTG ACTAGTAGCA TGAGATTTGG TTTGTCCCTA TTGAAACAAT AGGTATAGGG
          ②                                                    box II
-313 TGTGAAACAT TGAAACGTAA TTGACTCAAA TTCTCAAATA GGTTTCTTCA CCAAACTCCT
                                                            box II(reverse)
-253 CTTGTTTTGT CTAACAATCT TATATAGTCA CTAAAATAAT GTGTATAAAT TTTGCTACCG
              ①  ┌─Ndo I
-193 TCATTTAAAA GTTAGTGTCA TGAAACATAT GCCTCATTAT ATTTTATTAT TTTCGTTCAC
                                                AT·I box         Sau3A1┐
-133 TTTATTTCAA AGGCTTTAAA CTATATGACA TCATAACCAA AACAAGAATT AAAACGAGAT

- 73 CAATCAAACC CGTGTTGAAA CCTCAACTTG TGTCTAAATT GACCGTCACA AAAAAAAATC
     CAAT box         ┌─Isp(+1)              TATA box
- 13 TCACATCACA CCATCACTAA TAAATTTCCT TCTCCTTTCA AGTTGTAGCT AACTTATATA

+ 48 AGACATAAGC GTGCGAACCA GAGACAGAGA TAGAAATTGA GAGACGATAA GCAAAGTAGA

+108 AAACACAAGT TTCTCTCACA CACATTATCT CTTTCTCTAT TACCACCACT CATTCATAAC
                                                               ┌─Sac I
+168 AGAAACCCAC CAAAAAATAA AAAGAGAGAC TTTTCACTCT GGGGAGAGAG CTCAAGTTCT

+228 AATG
```

Initiation codon

SEQUENCE LISTING

```
<160> NUMBER OF SEQ ID NOS:  1

<210> SEQ ID NO 1
<211> LENGTH: 1084
<212> TYPE: DNA
<213> ORGANISM: Arabidopsis thaliana heynh

<400> SEQUENCE: 1
aaattcatgc ggaatcagag aacgttacca tggtgggatg aagatgaatt gcggccctgt     60 aaagtttag tcttgttcaa tagattgcac aaagaaagta aacaaacaac aacaaaaaaa    120
aagactgtag aaaagaaaaa aaaaaaggat aatcataacg gaatctttaa tttaccagcg    180
cgattaagga cctcagattg ttgttcggtg ccatgatcgg atattagggt tcgttcgctc    240
ttcttcttct ttgtctatac gcgatttgtg agaataaaaa aggtcggatc ttttgagagt    300
tctgtagttt aatgggctta tactattggg ccctagccca aatgagcgac actattgttc    360
attttgtaca aatctcttgg gctaatttat ttcaggctga ccaactaatt tggtcaacta    420
gttgggtttg gcatgtttaa tttcaatttc cacttggttc aattttttatg ttcaccgtcc    480 atgtaacttg actagtagca tgagatttgg tttgtcccta ttgaaacaat aggtataggg    540
tgtgaaacat tgaaacgtaa ttgactcaaa ttctcaaata ggtttcttca ccaaactcct    600
cttgttttgt ctaacaatct tatatagtca ctaaaataat gtgtataaat tttgctaccg    660
tcatttaaaa gttagtgtca tgaaacatat gcctcattat attttattat tttcgttcac    720
tttatttcaa aggcttaaaa ctatatgaca tcataaccaa aacaagaatt aaaacgagat    780
caatcaaacc cgtgttgaaa cctcaacttg tgtctaaatt gaccgtcaca aaaaaaaatc    840
tcacatcaca ccatcactaa taaatttcct tctccttcaa agttgtagct aacttatata    900
```

```
agacataagc gtgcgaacca gagacagaga tagaaattga gagacgataa gcaaagtaga        960
aaacacaagt ttctctcaca cacattatct ctttctctat taccaccact cattcataac       1020
agaaacccac caaaaaataa aaagagagac ttttcactct ggggagagag ctcaagttct       1080
aatg                                                                   1084
```

ELEMENT INDUCIBLE IN RESPONSE TO INJURY, A PROMOTER INDUCIBLE IN RESPONSE TO INJURY AND A TRANSGENIC PLANT

BACKGROUND OF THE INVENTION

1. Field of the Invention

This invention relates to a cis-element inducible in response to injury and derived from a promoter region of FAD7 of *Arabidopsis thaliana* Heynh.

2. Description of Related Art

Studies have confirmed the significant relationship between cold-resistance of a plant and the degree of unsaturation of fatty acids constructing biomembrane thereof. The inventors have experimentally indicated that a transformed-tobacco plant acquires higher-resistance against low temperatures by expressing a fatty acid desaturase, (unsaturating enzyme) gene FAD7, derived from *Arabidopsis thaliana,* in a high degree in the plant.

SUMMARY OF THE INVENTION

On the other hand, to produce certain protein in plant cells, a promoter, which exhibits constitutive expression and strong promoter activity, have been used. Such a promoter functions regardless of its external environmental conditions, sometimes providing economical losses in breeding a plant. For example, to improve the resistance of a plant against physical environmental stresses such insect damage, the use of various genes with resistant properties to the stresses is now investigated. That is, the resistance against injury might be improved by expressing ω-3 fatty acid desaturase enzyme by means of its constitutive promoter functioning in response to insect damage or physical damage.

Such particular expressed protein, however, is unnecessary for a plant under normal condition without injury. However, in the conventional gene expression system using a constitutive promoter, a plant is forced to express a particular protein, such as ω-3 fatty acid desaturase enzyme, unnecessary under normal condition.

Based on such background, it has been demanded to develop a promoter inducible in response to injury. For example, it is required to produce a breeding intermediate mother body, wherein the expression of a gene, which encodes ω-3 fatty acid desaturase enzyme or other proteins contributing to improving resistance of a plant against insect damage, may be induced in response to injury.

An object of the invention is to provide an element inducible in response to injury, which may be added to a promoter for developing a promoter inducible in response to injury.

Another object of the invention is to provide a means for developing a breed intermediate mother body with improved resistance against injury, by using a promoter provided with such element inducible in response to injury.

The invention provides an element inducible in response to injury, the element comprising (a) a base sequence referred to as nucleotide numbers from −430 to −363 in a sequence number 1 in a sequence list, or (b) a base sequence hybridizes with the base sequence (a) under stringent condition, the base sequence (b) being inducible in response to injury, or (b)' a base sequence (a), a part of which is deleted or substituted by another base sequence, or to which another base sequence is added, the base sequence (b)' being inducible in response to injury.

The invention provides an element inducible in response to injury, the element comprising (c) a base sequence referred to as nucleotide numbers from −242 to −223 in a sequence number 1 in a sequence list, or (d) a base sequence (d) hybridizes with the base sequence (c) under stringent condition, the base sequence (d) being inducible in response to injury, or (d)' a base sequence (c), a part of which is deleted or substituted by another base sequence, or to which another base sequence is added, the base sequence (d)' being inducible in response to injury.

The invention also provides an injury-inducible promoter characterized by containing each of the elements described above, and a transgenic plant comprising a recombinant DNA containing this injury-inductible promoter.

An ω-3 fatty acid desaturase enzyme catalyzes the final step of production of triene-fatty acids in a plant, which are main components of plant lipids. FAD7 derived from *Arabidopsis thaliana* is a gene encoding ω-3 fatty acid desaturase enzyme localized in chloroplast. FAD7 is specifically expressed in chloroplast organs and its expression is shown to be light-inducible.

Moreover, it is shown that localized damage on a plant body causes highly expression of FAD7, not only in chloroplast organs but also in non-chloroplast organs such as stalk or root. The invention identified a cis-element, in a promoter region of FAD7 gene, involved in organ-specific induction in response to injury, and therefore has an inventive step.

BRIEF DESCRIPTION OF DRAWINGS

The invention will be described with reference to the accompanying drawings, wherein:

FIG. 1 is a genome sequence of the promoter region derived from *Arabidopsis thaliana.

DETAILED DESCRIPTION OF EMBODIMENTS

The base sequence of FAD7 promoter region derived from *Arabidopsis thaliana* was already published by Nishiuchi et al (Nishiuchi et al. (1995) "Plant Mol. Biol" 29: 599–609). The base sequence of the promoter region is shown in a sequence list 1 described below and FIG. 1.

Parts of the promoter sequence were deleted to provide elements. The parts were selected from 5' upstream to each predetermined nucleotide number in a stepwise manner, as described below. Each element was ligated with a GUS gene of plasmid binary vector PbI101.1 (Clonetech) to provide each construct, which was incorporated into tobacco SR1 strain using leafdisc method mediated by agrobacterium (LBA4404) (Horsch et al. (1985) Science 227:1229–1231). Each reporter (GUS) activity of the R1 generation was measured.

Figure 2A:
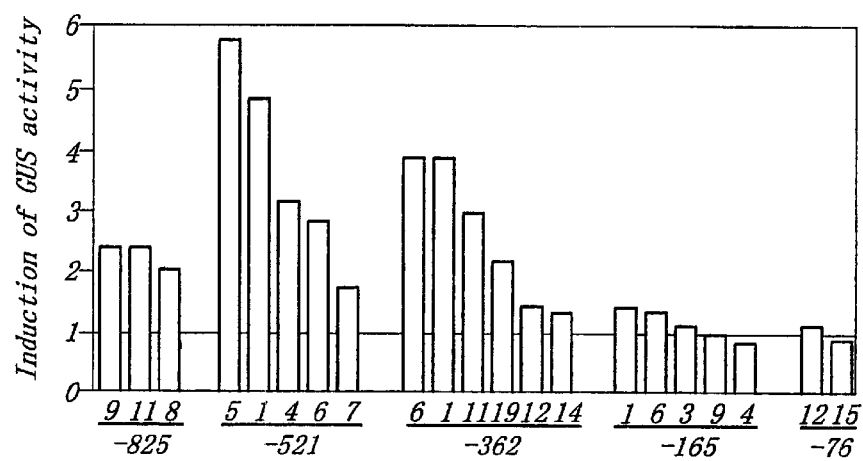
* and FIG. 2 is the experimental results on injury-inductivity of each element, which is a promoter region of FAD7 gene with a part of which being deleted. A: blade, B: stalk, C: root.
Figure 2B:
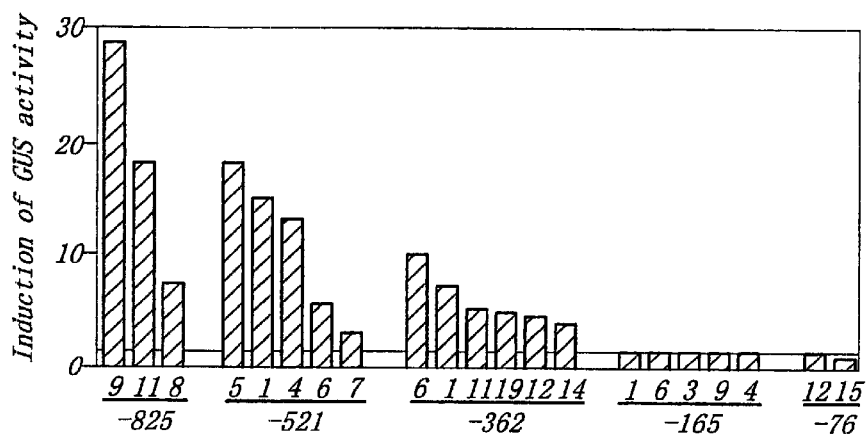
Figure 2C:
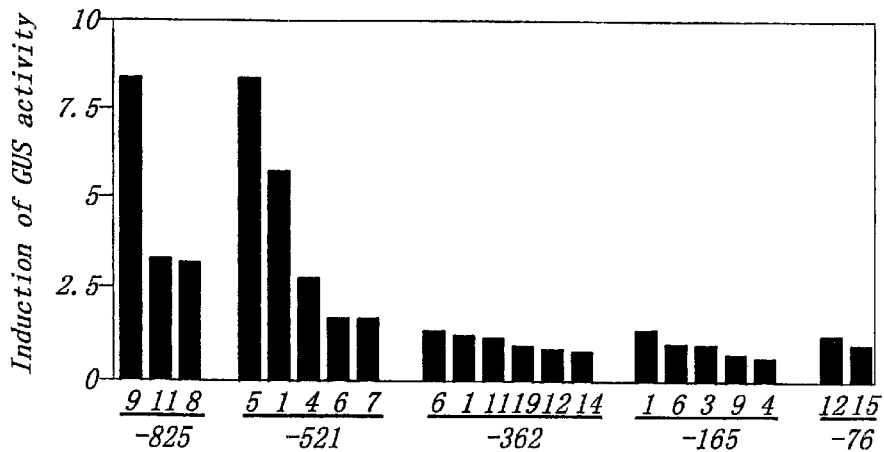

FIG. 2 shows the experimental results performed on A: blade, B: stalk and C: root. Each tobacco was planted in soil and cultivated for 3 months at 26° C. under continuous light illumination. As described above, a part of the promoter region was deleted to produce each element and construct.

Each deleted part is upstream of each predetermined nucleotide number indicated by each number in the lower column in the horizontal axis of each graph in FIG. 2. The numbers in the upper column in the horizontal axis of each graph in FIG. 2 indicate line numbers of R1 generation of tobacco used. The values in the vertical axis of each graph in FIG. 2 indicate the ratios of GUS activities measured in injured samples versus those measured in intact samples. In each line, each GUS activity is shown as an average measured in 5 plants.

As the result, in the case of blade and stalk (A, B), a region of nucleotide numbers from −259 to −197, and in the case of root (C), a region of nucleotide numbers from −520 to −363, are shown to be involved in injury-induced FAD7 gene expression.

Then, the existence of transcription factors that bind to these regions was investigated by gel-shift assay analysis (Green et al. (1989) "Plant Mol. Biol. Manual" BII, 1–22). On blade, stalk and root, gel shift assay was performed using nuclear proteins extracted from an intact tissue and an injured tissue and DNA probes corin response to various base sequences of the regions described above. As a result, on blade and stalk, a band mobility shift in response to injury was detected by electrophoresis using a base sequence of −242/−223. (TAACAATCTTATATAGTCAC) as a probe. The organ-specific injury inductivity on blade and stalk was diminished when FAD7 promoter, in which the base sequence was deleted, was ligated to a GUS gene and incorporated into tobacco plant.

On root, a band shifting in response to injury was detected by electrophoresis, when a base sequence of −430/−363 was used as a probe. The organ-specific injury inductivity in root was diminished, when FAD7 promoter, in which the base sequence was deleted, was ligated to a GUS gene and incorporated into a tobacco plant.

Accordingly, it was indicated that these sequences functioned as cis-elements. Moreover, an element of −430/−363 responded to jasmonate, proving that it exists at the end of octadecanoid intracellular signal transmission pathway. An element of −242/−223 did not respond to jasmonate, proving that it exists at the end of a signal transmission pathway different from the octadecanoid intracellular signal transmission pathways.

In this invention, a plasmid can be used as a vector to construct a recombinant DNA. A preferred plant to incorporate such recombinant DNA includes monocotyledon useful cultivated plants such as maize, rice, wheat, barely, oat, millet, barnyard millet and tobacco. In various injury-responsive elements, even if one or several bases of the above described element is deleted, substituted or to which another nucleotide base sequence is added, it is in the range of this invention, so far as the injury-inducible function of the element was preserved. Moreover, the injury-inductive element of this invention may induce the production of various proteins including ω-3 fatty acid desaturase enzyme and protease inhibitor II.

What is claimed is:

1. An isolated nucleic acid consisting of nucleotides 611 to 629 of SEQ ID NO:1.

2. The isolated nucleic acid according to claim 1 being derived from a promoter region of FAD7 of *Arabidopsis thaliana* Heynh.

3. A transgenic plant comprising a recombinant DNA comprising the isolated nucleic acid as claimed in claim 1 operably linked to a heterologous promoter sequence.

4. The transgenic plant as claimed in claim 3, wherein the element is inducible in response to injury in a blade or a stalk of the plant.

5. The transgenic plant as claimed in claim 3, being a monocotyledonous useful cultivated plant.

6. The transgenic plant as claimed in claim 5, wherein the monocotyledonous useful cultivated plant is selected from a group consisting of maize, rice, wheat, barley, oat, millet, barnyard millet and tobacco.

7. The transgenic plant as claimed in claim 3, wherein the element induces the production of a protein selected from a group consisting of ω-3 fatty acid desaturase enzyme and protease inhibitor II.

8. A method of inducing expression in response to injury in a plant, comprising incorporating into the plant an element inducible in response to injury comprising a base sequence of nucleotide numbers from 611 to 629 of SEQ ID NO: 1 operably linked to a heterologous promoter sequence.

* * * * *